US005776765A

United States Patent [19]
Graham et al.

[11] Patent Number: 5,776,765
[45] Date of Patent: Jul. 7, 1998

[54] METHOD FOR PREPARING A PHARMACEUTICALLY ACTIVE ENANTIOMERIC OR ENANTIOMERICALLY ENRICHED SULFOXIDE COMPOUND BY ENANTIOSELECTIVE BIOREDUCTION OF A RACEMATE SULFOXIDE COMPOUND

[75] Inventors: Daniel Graham, Childwall Valley; Robert Holt, Fleetham, both of United Kingdom; Per Lindberg, Mölndal, Sweden; Stephen Taylor, Darlington, United Kingdom

[73] Assignee: Astra Aktiebolag, Sodertalje, Sweden

[21] Appl. No.: 569,083

[22] PCT Filed: Nov. 27, 1995

[86] PCT No.: PCT/SE95/01416

§ 371 Date: Dec. 18, 1995

§ 102(e) Date: Dec. 18, 1995

[87] PCT Pub. No.: WO96/17077

PCT Pub. Date: Jun. 6, 1996

[30] Foreign Application Priority Data

Nov. 28, 1994 [GB] United Kingdom ............ 9423968

[51] Int. Cl.$^6$ .................... C12P 11/00; C07D 401/12
[52] U.S. Cl. ................ 435/280; 435/122; 435/130; 435/822; 435/849; 435/873; 546/273.4; 546/273.7
[58] Field of Search .............. 546/273.4, 273.7; 435/130, 122, 280, 822, 873, 849

[56] References Cited

U.S. PATENT DOCUMENTS

| | | | |
|---|---|---|---|
| 4,873,337 | 10/1989 | Sih et al. | 546/271 |
| 5,274,099 | 12/1993 | Brandstroom et al. | 546/273.7 |

FOREIGN PATENT DOCUMENTS

| | | | |
|---|---|---|---|
| 0005129 | 4/1981 | European Pat. Off. | 546/273.4 |
| 0166287 | 6/1984 | European Pat. Off. | 546/273.4 |
| 0124495 | 1/1987 | European Pat. Off. | 546/273.7 |
| 0174726 | 4/1989 | European Pat. Off. | 546/273.7 |
| 4035455 | 5/1992 | Germany | 546/273.7 |
| 92/08716 | 5/1992 | WIPO | 546/273.7 |
| 96/17076 | 6/1996 | WIPO . | |
| 96/17077 | 6/1996 | WIPO . | |

OTHER PUBLICATIONS

Abo et al. (1997) "Preparative asymmetric deoxygenation of alkyl aryl sulfoxides . . ." Tetrahedron: Asymmetry 8:345.
Erlandsson (1990) "Resolution of the enantiomers of omeprazole and . . ." Journal of Chromatography 532: 305–319.
Cashman, J.R. et al. 1993 "Chemical, enzymatic and Human enditioselective S–oxygenation" Drug Metabolism and Dispostion 21:587.

(List continued on next page.)

*Primary Examiner*—Floyd D. Higel
*Attorney, Agent, or Firm*—White & Case L.L.P.

[57] ABSTRACT

A compound of formula (II), either as a single enantiomer or in an enantiomerically enriched form

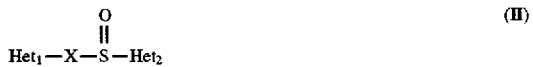

wherein:

Het$_1$ is

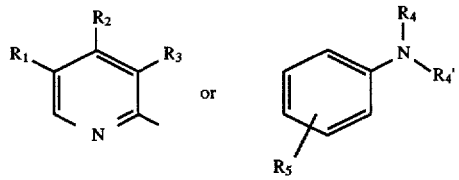

and
Het$_2$ is

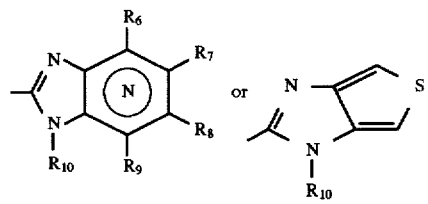

and

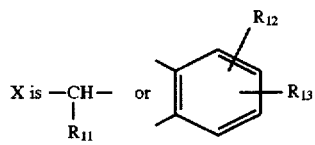

(wherein N in the benzimidazole moiety of Het$_2$ means that one of the carbon atoms substituted by any one of R$_6$ to R$_9$ optionally may be exchanged for an unsubstituted nitrogen atom; R$_1$, R$_2$ and R$_3$ are the same or different and selected from hydrogen, alkyl, alkoxy optionally substituted by fluorine, alkylthio, alkoxyalkoxy, dialkylamino, piperidino, morpholino, halogen, phenylalkyl, phenylakoxy; R$_4$ and R$_4'$ are the same or different and selected from hydrogen, alkyl, aralkyl; R$_5$ is hydrogen, halogen, trifluoromethyl, alkyl, alkoxy; R$_6$-R$_9$ are the same or different and selected from hydrogen, alkyl, alkoxy, halogen, haloalkoxy, alkylcarbonyl, alkoxycarbonyl, oxazolyl, trifluoroalkyl or adjacent groups R$_6$-R$_9$ may complete together with the carbon atoms to which they are attached optionally substituted ring structures; R$_{10}$ is hydrogen or alkoxycarbonyloxymethyl; R$_{11}$ is hydrogen or forms an alkylene chain together with R$_3$; R$_{12}$ and R$_{13}$ are the same or different and selected from hydrogen, halogen or alkyl) is obtained by stereoselective bioreduction of a compound of formula (II) in racemic form.

9 Claims, No Drawings

OTHER PUBLICATIONS

Kashiyama et al. 1994 "Chiral inversion of drug: . . ." Biochem. Pharmacology 48:237.

Biosci. Biotech. Biochem., (1994) 58, pp. 596–597, Abo et al.

J. Chromatography, 532 (1990), pp. 305–319, Erlandsson et al.

METHOD FOR PREPARING A PHARMACEUTICALLY ACTIVE ENANTIOMERIC OR ENANTIOMERICALLY ENRICHED SULFOXIDE COMPOUND BY ENANTIOSELECTIVE BIOREDUCTION OF A RACEMATE SULFOXIDE COMPOUND

This application is a 371 of PCT/SE 95/01416 field Nov. 27, 1995.

The present invention relates to a method of obtaining compounds as defined below, either as a single enantiomer or in an enantiomerically enriched form.

BACKGROUND OF THE INVENTION

The racemic form of the compounds prepared by the method of the present invention are known compounds. Some of the compounds are also known in single enantiomeric form. The compounds are active $H^+K^+$ATPase inhibitors and they, including their pharmaceutically acceptable salts, are effective acid secretion inhibitors, and known for use as anti ulcer agents. The compounds, which include the known compounds omeprazole (compound of formula (IIa) below), Iansoprazole (compound of formula (IIc) below) and pantoprazole (compound of formula (IIb) below), are known for example from European Patent specifications EP 5129 and 124495, EP 174726 and EP 166287.

These compounds, being sulfoxides, have an asymmetric centre in the sulfur atom, i.e. exist as two optical isomers (enantiomers). It is desirable to obtain compounds with improved pharmacokinetic and metabolic properties which will give an improved therapeutic profile such as a lower degree of interindividual variation.

The separation of enantiomers of omeprazole in analytical scale is described in e.g. J. Chromatography, 532 (1990), 305-19. Also the separation of enantiomers of compounds with which the present invention is concerned, including omeprazole and pantoprazole, is described in German Patent Specification DE 4035455.

Recently there has been a great deal of literature published relating to the synthesis of optically active compounds using biocatalysts. The majority of this work has been aimed at finding routes to single enantiomer forms of pharmaceuticals. The reactions receiving most attention have been those involved in the preparation of esters, acids and alcohols due to the general utility of these funtionalities in synthesis and also because the biocatalysts are readily available.

Studies on the synthesis of optically active sulfoxides are relatively rare partly due to the small number of pharmaceuticals containing sulfoxide groups and partly due to the fact that enzymes that react with the sulphur centre are not available commercially. The enantioselective reduction of methylphenylsulfoxide to the sulfide has been discussed by Abo M., Tachibana M., Okubo A. and Yamazaki S. (1994) Biosci. Biotech. Biochem. 596-597.

DESCRIPTION OF THE INVENTION

According to the present invention there is provided a method of obtaining a compound of formula (II) either as a single enantiomer or in an enantiomerically enriched form:

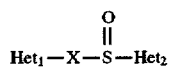

wherein:

$Het_1$ is

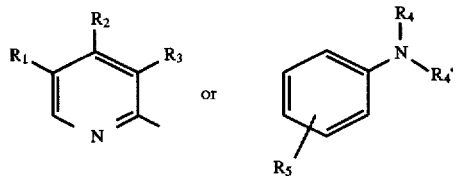

and $Het_2$ is

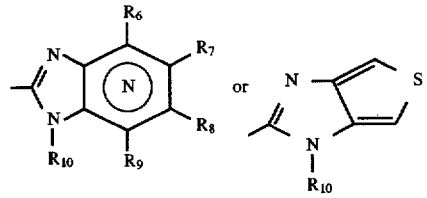

and

X is

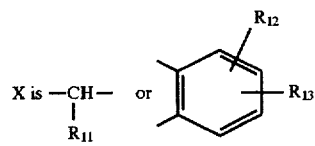

wherein:

N in the benzimidazole moiety of $Het_2$ means that one of the carbon atoms substituted by any one of $R_6$ to $R_9$ optionally may be exchanged for an unsubstituted nitrogen atom;

$R_1$, $R_2$ and $R_3$ are the same or different and selected from hydrogen, alkyl, alkoxy optionally substituted by fluorine, alkylthio, alkoxyalkoxy, dialkylamino, piperidino, morpholino, halogen, phenylalkyl, phenylalkoxy;

$R_4$ and $R_{4'}$ are the same or different and selected from hydrogen, alkyl, aralkyl;

$R_5$ is hydrogen, halogen, trifluoromethyl, alkyl, alkoxy;

$R_6$–$R_9$ are the same or different and selected from hydrogen, alkyl, alkoxy, halogen, haloalkoxy, alkylcarbonyl, alkoxycarbonyl, oxazolyl, trifluoroalkyl or adjacent groups $R_6$–$R_9$ may complete together with the carbon atoms to which they are attached optionally substituted ring structures;

$R_{10}$ is hydrogen or alkcoxycarbonyloxymethyl;

$R_{11}$ is hydrogen or forms an alkylene chain together with R;

$R_{12}$ and $R_{13}$ are the same or different and selected from hydrogen, halogen or alkyl;

which method comprises stereoselective bioreduction of a compound of formula (II) in racemic form.

The compounds of formula (II) are active $H^+K^+$APTase inhibitors.

The compounds of formula (II) possess a stereogenic (asymmetric) centre which is the sulphur atom which forms the sulfoxide group between the $Het_1$ -X-and $Het_2$ moieties. The compounds of formula (II) generally are a racemic mixture initially.

In the method according to the present invention the starting compound of formula (II) in racemic form is stereoselectively bioreduced to the corresponding sulfide of the formula:

Het₁—X—S—Het₂                                    (I)

(wherein Het₁, X and Het₂ are as defined above). Thus there is obtained compound of formula (II) as a single enantiomer or in enantiomerically enriched form which may be separated from the sulfide produced.

In the above definitions allyl groups or moieties may be branched or straight chained or comprise cyclic alkyl groups, for example cycloalkylalkyl.

Preferably:
Het₁ is

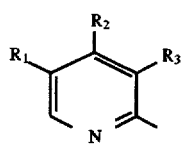

and
Het₂ is

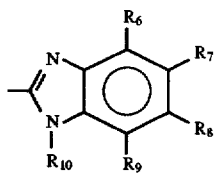

and
X is

(wherein R₁, R₂, R₃, R₆ –R₉, R₁₀ and R₁₁ are as defined above).

Most preferably the compounds with which the method of the present invention is concerned are compounds of the formula (IIa) to (IIe):

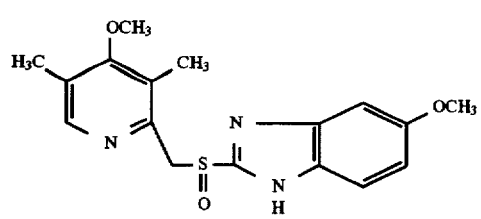
(IIa)

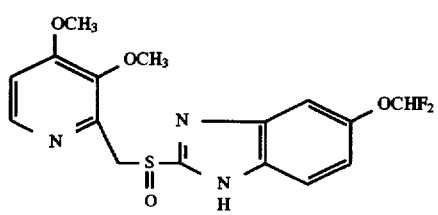
(IIb)

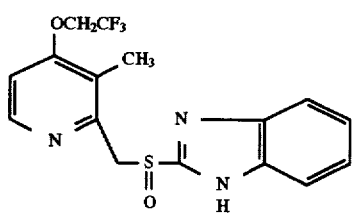
(IIc)

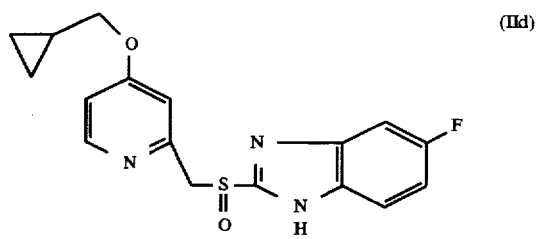
(IId)

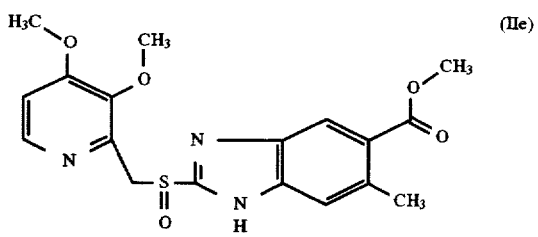
(IIe)

An example of a compound of formula (II) wherein R₁₀ is alkoxycarbonyloxymethyl is

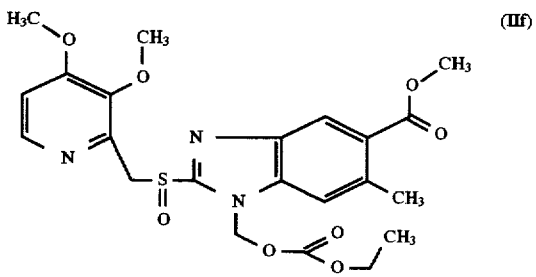
(IIf)

The sulfides formed from the compounds (IIa)-(IIf) will be respectively

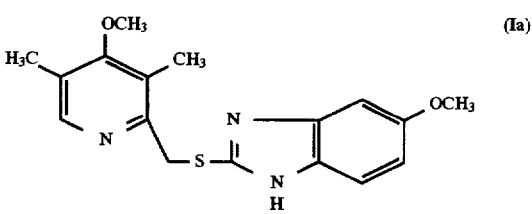
(Ia)

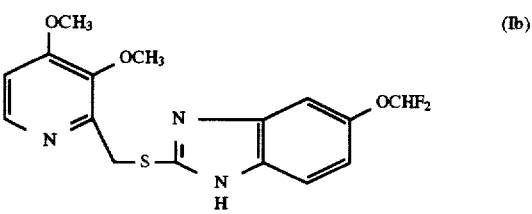
(Ib)

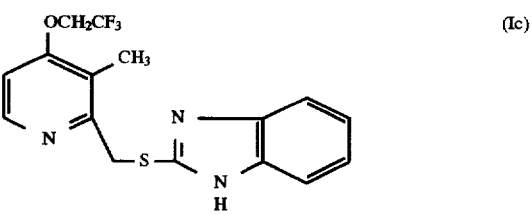
(Ic)

-continued

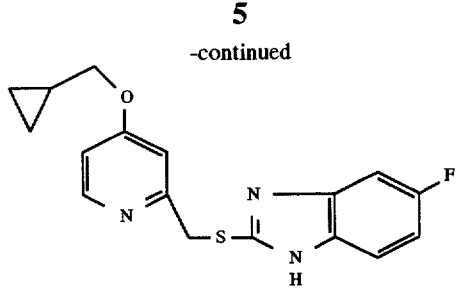
(Id)

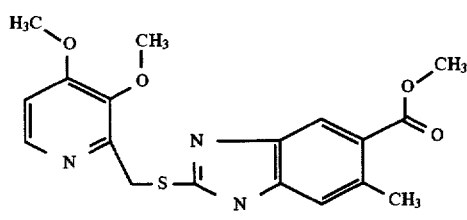
(Ie)

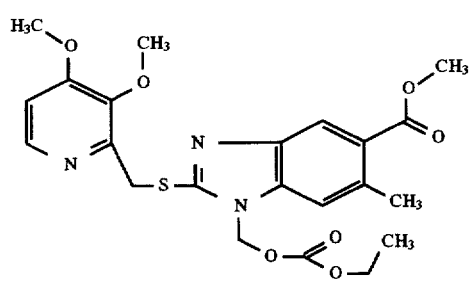
(If)

The stereoselective bioreduction according to the present invention may be carried out using a microorganism or an enzyme system derivable therefrom. The organisms used in the method according to the present invention are suitably organisms containing DMSO reductase, for example enterobacteriaceae such as *E. Coli* and *Proteus sp.*, and purple non-sulfur bacteria of the genus Rhodobacter.

Also there may be used DMSO reductase to effect the bioreduction.

Using DMSO reductase, under anaerobic conditions a cofactor flavin adenine dinudeotide (FAD) or flavin mononudeotide (FMN) for example may be photoreduced in the presence of ethylene diamine tetraacetic acid (EDTA). The re-oxidation of the FAD or FMN is coupled to the reduction of the sulfoxide via the DMSO reductase. Hence an artificial biocatalytic cycle is generated in the absence of the cells natural anaerobic electron transport mechanism.

Photo catalysed DMSO Reductase Reaction

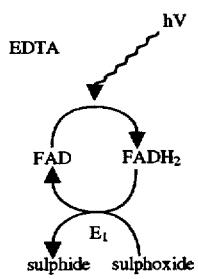

$E_1$ - DMSO reductase

The compounds of formula (II) are generally add labile and thus the use of acid conditions is to be avoided. Generally the method according to the invention may be carried out at a pH of 7.6 to 8, suitably about 7.6, and at temperature of 25° to 35° C., suitably about 28° C.

According to one embodiment of the invention the method comprises contacting the compound of formula (II) with a microorganism which is:

*Proteus vulgaris*
*Proteus mirabilis*
*Escherichia coli*
*Rhodobacter capsulatus*

The microorganisms used are preferably:

*Proteus vulgaris* NCIMB 67
*Proteus mirabilis* NCIMB 8268
*Escherichia coli* ATCC 33694
*Rhodobacter capsulatus* DSM 938

These microorganisms are available from the following culture collections.

NCIMB
National Collection Of Industrial And Marine Bacteria
23 Saint Machar Drive
Aberdeen AB2 1RY
United Kingdom ATCC
American Type Culture Collection
12301 Parklawn Drive
Rockville Maryland 20852
United States of America DSM
Deutsche Sammlung von Mikroorganismen
Mascheroder Weg 1b
D-38124
Braunschweig
Germany The present invention will now be illustrated with reference to the Examples.

EXAMPLE 1

The reductive resolution of the compound of formula (IIa) was investigated using whole cells of *E. Coli* ATCC 33694, *Proteus vulgaris* NCIMB 67, *Proteus mirabilis* NCIMB 8268 and a preparation of DMSO reductase from *Rhodobacter Capsulatus* DSM 938. *E. Coli* and the two strains of *Proteus* were grown under essentially anaerobic conditions in 1 litre screw capped flasks containing 800 ml of medium at 35° C. for 48 hours on a rotary shaker. The basal culture medium used had the following composition (g/l): $NaH_2PO_4$, 1.56; $K_2HPO_4$, 1.9; $(NH_4)_2SO_4$, 1.8; $MgSO_4\cdot 7H_2O$, 0.2; $FeCl_3$, 0.005; $Na_2MoO_4\cdot 2H_2O$, 0.001; casamino acids, 1.5. After autoclaving this was supplemented with the following components (g/l): glycerol (for *Escherichia coli*) or glucose (for *Proteus mirabilis* ), 5; thmine·HCl, 0.03; nicotinic acid, 0.007. Dimethylsulfoxide (70 mM) was added to the medium to serve as terminal electron acceptor for anaerobic respiration and as inducer for dimethylsulfoxide (DMSO) reductase. Trace elements solution (1 mi/litre) was also added to the medium. The stock trace elements solution contained (g/l): $CuSO_4\cdot 5H_2O$, 0.02; $MnSO_4\cdot 4H_2O$, 0.1; $ZnSO_4\cdot 7H_2O$, 0.1; $CaCO_3$, 1.8. *E. Coli* was also grown anaerobically on the same medium under the same conditions but with 40 mM of fumarate as electron acceptor.

Cells were harvested by centrifuging and washed twice in 10 mM phosphate buffer, pH 7.6. The cells were then resuspended in 100 mM phosphate buffer, pH 7.6 to give a dry cell weight concentration of 3–6 g/l.

50 ml of each cell suspension was then placed in an autotitrator vessel and stirred without aeration in the presence of 0.1–0.3 g/l substrate and glucose (2.5%) at 35° C. The pH was maintained at 7.6 by autotitration with 0.5 mM NaOH.

Cells of *Rhodobacter capsulatus* DSM 938 where grown and DMSO reductase enzyme prepared as describes in Example 2. below. The reductive resolution of the compound of formula (IIa) using said enzyme preparation was then carried out as describes in Example 2. except that the compound of formula (IIa) was present at a substrate concentration of 2.9 mM.

Detection of Products

The bioreduction of the compound of formula (IIa) was followed by reverse phase HPLC on a Spherisorb S5-ODS2 reverse phase column eluted with a 50:50 mixture of acetonitrile and 25 mM sodium phosphate buffer. pH 7.6 at a flow rate of 0.8 ml/mirL Under such conditions the compounds of formula (IIa) and (Ia) were well resolved with retention times of 5.2 and 9.8 minutes respectively. Both compounds were detected at a wavelength of 300 nm.

The enantiomeric composition of the compound of formula (IIa) remaining was investigated by the following method. After removal of biomass the aqueous media was extracted with two volumes of ammonia saturated dichloromethaie. The pooled organic extracts were dried over anhydrous sodium sulfate and the solvent was evaporated under reduced pressure to afford a pale brown solid. Then the enantiomeric composition of sulfoxide was determined by HPLC on a Chiralpak AD Column under the following conditions:

Column Chiralpack AD 250 mm×4.6 mm interior diameter with 50 mm guard column
Eluent Hexane:Ethanol:Methanol (40:55:5% V/V)
Flow 1.0 ml/min
Injection Volume 20 μl
Wavelength 300 nm
Retention times
Compound of formula (Ia) 5.1 min
Compound of formula (IIa)
(+) Enantiomer 8.5 min
(−) Enantiomer 13.4 min The result in Table 1 were obtained for *E. Coli* ATCC 33694:

TABLE 1

| Electron Acceptor | Dry Cell Weight g/l | Time (min) | Compound of formula (IIa) (ppm or mg L⁻¹) | Compound of formula (Ia) (ppm or mg L⁻¹) | ee % (+) | E |
|---|---|---|---|---|---|---|
| Fumarate | 6 | 0 | 76 | 0 | — | — |
| | | 5 | 65 | 10 | — | — |
| | | 15 | 42 | 33 | — | — |
| | | 30 | 33 | 42 | — | — |
| | | 40 | 30 | 45 | — | — |
| | | 65 | 27 | 47 | — | — |
| | | 90 | 25 | 50 | — | — |
| | | 130 | 22 | 53 | >99 | 11 |
| DMSO | 6 | 0 | 74 | 0 | 0 | — |
| | | 15 | 47 | 22 | 28 | — |
| | | 35 | 40 | 34 | 74 | — |
| | | 45 | 34 | 38 | 90 | 20 |

In the above Table E is the enantiospecificity constant which may be determined from the extent of conversion and enantiomeric excess of the unreacted compound from the following equation:

$$E = \frac{\ln[(1-C)\times(1-ee_s)]}{\ln[(1-C)\times(1+ee_s)]}$$

where C=conversion $ee_s$ =enantiomeric excess of the unreacted compound.

Also in the above table ee is the enantiomeric excess value for the (+) enantiomer of the compound of formula (IIa). The enantiomeric excess value gives an indication of the relative amounts of each enantiomer obtained. The value is the difference between the relative percentages for the two enantiomers. Thus, for example, when the percentage of the (−) enantiomer of the remaining sulfoxide is 97.5% and the percentage for the (+) enantiomer is 2.5%, the enantiomeric excess for the (−) enantiomer is 95%.

At a starting concentration of 0.3 g/l both *P. vulgaris* NCIMB 67 and *P. mirabilis* NCIMB 8268 afforded the (+) enantiomer of the compound of formula (IIa) in >99% enantiomeric excess after 48 h (Table 2) in yields of 32% and 5% respectively.

TABLE 2

| | *P. vulgaris* NCIMB 67 Ratio of Enantiomers | | *P. mirabilis* NCIMB 8268 Ratio of Enantiomers | |
|---|---|---|---|---|
| Time hours | (+) | (−) | (+) | (−) |
| 0 | 50 | 50 | 50 | 50 |
| 24 | 79 | 21 | 67 | 33 |
| 48 | >99 | <1 | >99 | <1 |

The final concentration of the compound of formula (IIa) after 48 hours was 48 mg/litre for *P. vulgaris* NCIMB 67 and 8 mg/litre for *P. mirabilus* NCIMB 8268.

At a lower starting concentration of 0.1 g/l both organisms again afforded the (+) enantiomer of the compound of formula (IIa) in >99% enantiomeric excess, but after 24 hr (Table 3A) in 44% and 40% yields for *P. vulgaris* NCIMB 67 and *P. mirabilis* NCIMB 8268 respectively.

TABLE 3A

| | *P. vulgaris* NCIMB 67 Ratio of Enantiomers | | *P. mirabilis* NCIMB 8268 Ratio of Enantiomers | |
|---|---|---|---|---|
| Time hours | (+) | (−) | (+) | (−) |
| 0 | 50 | 50 | 50 | 50 |
| 5 | 78 | 22 | 79 | 21 |
| 24 | >99 | <1 | >99 | <1 |

The final concentration of the compound for formula (IIa) after 24 hours was 22 mg/litre of *P. vulgaris* NCIMB 67 and 20 mg/litre for *P. mirabilis* NCIMB 8268.

The compound of formula (IIa) acts as a substrate for the isolated DMSO reductase from *Rhodobacter capsulatus* as shown in Table 3B. The conversion of total suloxide after 15 minutes and after 1 hour was 80% and >90% respectively.

TABLE 3B

| | R. capsulatus DSM 938 Ratio of Enantiomers | |
|---|---|---|
| Time | (+) | (−) |
| 0 | 50 | 50 |
| 15 minutes | 50 | 50 |
| 1 h | 15 | 85 |

EXAMPLE 2

The reductive resolution of compounds of formula (IIb) and (IIc) was investigated with E. coli ATCC 33694, P. vulgaris NCIMB 67, and a preparation of DMSO reductase from R. capsulatus DSM 938. The reaction conditions were as described in Example 1 for E. coli and P. vulgaris except the compounds of formula (IIb) and (IIc) were present at a substrate concentration of 0.1 g/l. Where a preparation of DMSO reductase was used, the reaction conditions were as follows:

Cells of R. capsulatus DSM 938 were grown phototrophically in 25l carboys containing RCV medium supplemented with 50 mM DMSO between two banks of 100 W tungsten bulbs. Cells were harvested by cross-flow filtration followed by centrifugation at 10,000 rpm in a Beckman GSA rotor for 30 min. The pellets were washed once with 50 mM Tris/HCl pH 8.0 and resuspended to approximately 2 g/ml in 50 mM Tris/HCl pH 8.0+0.5 M sucrose and 1.5 mM EDTA (STE buffer). Lysozyme was added at 0.6 mg/ml and the suspension (approx 1l) was stirred at 30° C. for 15 min. After centrifugation as described above the supernatant (periplasmic fraction) was decanted off and brought to 50% saturation with ammonium sulphate. Following centrifugation the supernatant was brought to 70% saturation and recentifuged. The 50–70% pellet was resuspended in a minimum volume of 50 mM Tris/HCl pH 8.0 and dialysed against 3×100 volumes of the same buffer being concentrated to approx 5 ml by ultra-filtration through an Amicon PM 10 membrane. The concentrated sample was brought to 150 mM NaCl, charged onto a Sephacryl S200 gel filtration column (column vol=510 ml) and eluted with 700 ml of 50 mM Tris/HCl pH 8.0+150 mM NaCl. Peak enzyme activity eluted at approx 320 ml (data not shown) and peak fractions were pooled and concentrated as above.

The "RCV" medium used in this Example had the following composition (g per litre of deionised water or as mM):
Propionate 30 mM
$(NH_4)_2SO_4$ 1 g
$KPO_4$ buffer 10 mM
$MgSO_4 \cdot 7H_2O$ 120 mg
$CaCl_2 \cdot 2H_2O$ 75 mg
Sodium EDTA 20 mg
$FeSO_4 \cdot 7H_2O$ 24 mg
Thiamine hydrochloride 1 mg
Trace element soln. 1 ml
Trace element solution (per 250 ml)
$H_3BO_3$ 0.7 g
$MnSO_4 \cdot H_2O$ 398 mg
$Na_2MoO_4 \cdot 2H_2O$ 188 mg
$ZnSO_4 \cdot 7H_2O$ 60 mg
$Cu(NO_3)_2 \cdot 3H_2O$ 10 mg The puzified DMSO reductase from Rhodobacter capsulatus DSM 938 was used in the photo-catalysed assay for the reduction of sulfoxide. A 5 ml gas-tight syringe was filled with approx 3 ml of degassed assay buffer, 50 mM Tris/HCl, 10 mM EDTA, pH 8.0. Flavin mononudeotide (FMN) and sulfoxide were added to the syringe to give final concentrations of 250 µM and 0.3 mM respectively (based on a final volume of 5 ml). The FMN was then reduced via illumination with a tungsten lamp. The DMSO reductase sample (2–10 mg: 2–10 µM) was then added to the solution and the volume made up to 5 ml with degassed buffer. The syringe was then illuminated as before. A 1 ml sample was removed immediately (t=o) and subsequent sampling repeated over the desired timecourse.

Detection of Products

The bioreduction of the compounds of formula (IIb) and (IIc) was followed by reverse phase HPLC as described in Example 1 except that the retention times were as follows:

TABLE 4

| Compound of Formula | Retention Time (min) |
|---|---|
| Ib | 8.1 |
| IIb | 4.2 |
| Ic | 10.5 |
| IIc | 5.7 |

The enantiomeric composition of the compounds of formula (IIb) and (IIc) remaining was investigated by the method of Example 1 except that in he chiral HPLC step, the solvent composition, flow rate and retention time were as follows:

TABLE 5

| Compound of Formula | Solvent Composition | Flow Rate (ml/min) | Retention time (min) |
|---|---|---|---|
| IIb | Hexane/Ethanol (70:30% v/v) | 1.0 | 32.3 (Enantiomer A) 36.6 (Enantiomer B) |
| IIc | Hexane/Ethanol (70:30% v/v) | 0.5 | 34.3 (Enantiomer A) 36.3 (Enantiomer B) |

The enantiomer which eluted first is referred to as enantiomer A and the second as enantiomer B.
The following results were obtained:

TABLE 6

| Biocatalyst | Time (hr) | Ratio of enantiomers of formula (IIb) A | B | Conversion (%) |
|---|---|---|---|---|
| E coli ATCC 33694 | 0 | 50 | 50 | — |
| | 2 | 45 | 55 | 68 |
| | 20 | 40 | 60 | — |
| | 44 | <1 | >99 | 89 |
| P vulgaris NCIMB 67 | 0 | 50 | 50 | — |
| | 2 | 53 | 47 | 75 |
| | 6 | 53 | 47 | 75 |
| | 48 | 53 | 47 | 75 |

Conversion values were for the percentage conversion of the compound of formula (IIb) to the compound of formula (Ib).

TABLE 7

| Biocatalyst | Time (hr) | Ratio of enantiomers of formula (IIc) A | Ratio of enantiomers of formula (IIc) B | Conversion (%) |
|---|---|---|---|---|
| E. Coli ATCC 33694 | 0 | 50 | 50 | — |
|  | 2 | 39 | 61 | 83 |
|  | 20 | 21 | 79 | 96 |
| P. Vulgaris NCIMB 67 | 0 | 50 | 50 | — |
|  | 2 | 40 | 60 | 45 |
|  | 6 | 40 | 60 | 54 |
|  | 48 | 38 | 62 | 85 |
| DMSO reductase (R. capsulatus DSM 938) | 0 | 50 | 50 | — |
|  | 0.25 | 41 | 59 | 31 |
|  | 1.5 | 41 | 59 | 54 |

Conversion values were the percentage conversion of the compound of formula (IIc) to compound of formula (Ic).

EXAMPLE 3

The reductive resolution of compounds of formula (IId) and (IIe) was investigated.

E. coli ATCC 33694 and Proteus mirabilis NCIMB 8268 were screened for the reductive resolution of compounds of formula (IId) and (IIe). Both organisms were grown anaerobically with fumarate as terminal electron acceptor and glycerol (E. coli) or glucose (Proteus mirabilis) as carbon source according to the method of Example 1. After 48 hrs growth at 35° C. the cells were harvested by centrifuging at 8k rpm and 4° C. and washed by resuspending in 10 mM sodium phosphate buffer, pH 7.6 and centrifuging as above. The cells were finally resuspended in 100 mM sodium phosphate buffer, pH 7.6. The dry cell weights were 8 g/l (E. coli) and 4.5 g/l (Proteus mirabilis) for the compound of formula (IId) and 4.3 g/l (E. coli) and 3.9 g/l (Proteus mirabilis) for the compound of formula (IIe). The reductive resolution of the compounds of formula (IId) and (IIe) was investigated in an autotitrator containing 40 ml cell suspension, 100 ppm of either substrate and 1% w/v glucose as energy source.

Detection of Products

The bioreduction of the compounds of formula (IId) and (IIe) was followed by reverse phase HPLC as described in Example 1 except that the retention times were as follows:

TABLE 8

| Compound of formula | Retention Time (min) |
|---|---|
| Id | 13.7 |
| IId | 5.0 |
| Ie | 9.4 |
| IIe | 4.3 |

The enantiomeric composition of the compounds of formula (IId) and (IIe) remaining was investigated by the method of Example 1 except that in the chiral HPLC step, the solvent composition, flow rate and retention time were as follows:

TABLE 9

| Compound of Formula | Solvent Composition | Flow Rate (ml/min) | Retention Time (min) |
|---|---|---|---|
| IId | Hexane/Ethanol (70:30% v/v) | 1.0 | 12.9 (Enantiomer A) |
|  |  |  | 21.7 (Enantiomer B) |
|  | Hexane/Ethanol/Methanol (40:55:5% v/v) | 1.0 | 7.4 (Enantiomer A) |
|  |  |  | 10.6 (Enantiomer B) |
| IIe | Hexane/Ethanol (70:30% v/v) | 1.0 | 26.0 (Enantiomer A) |
|  |  |  | 30.5 (Enantiomer B) |

The enantiomer which eluted first is referred to as enantiomer A and the second as enantiomer B.

The results for the reduction of the compound of formula (IId) by both E. coli ATCC 33694 and P. mirabilis NCIMB 8268 were as follows:

TABLE 10

| Microorganism | Conversion (%) | Enantiomeric excess (%) | Enantiomer | E |
|---|---|---|---|---|
| E. Coli ATCC 33694 | 79 | 88 | B | 4 |
| P. mirabilis NCIMB 8268 | 66 | 90 | B | 8 |

The conversion values were for the percentage conversion of compound of formula (IId) to compound of formula (Id).

The reduction of the compound of formula (IIe) by E. coli and P. mirabilis afforded 'B' enantiomer in high enantiomeric excess.

TABLE 11

| Microorganism | Conversion (%) | Enantiomeric excess (%) | Enantiomer | E |
|---|---|---|---|---|
| E. Coli ATCC 33694 | 78 | 98.2 | B | 7 |
| P. mirabilis NCIMB 8268 | 70 | >99 | B | 11 |

The conversion values were for the percentage conversion of the compound of formula (IIe) to the compound of formula (Ie).

These conversion figures were determined from the aqueous dissolved concentration of sulfoxide at the end of the reaction. The magnitude of the enantiospecificity constant is similar to that obtained for the reductive resolution of the compound of formula (IIa) by E. coli ATCC 33694 and Proteus mirabilis NCIMB 8268.

We claim:

1. A method of obtaining a pharmaceutically active compound as a single sulfoxide enantiomer or an enantiomerically enriched sulfoxide form having the formula (II):

wherein:

Het₁ is

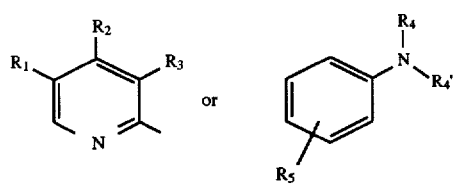

and
Het₂ is

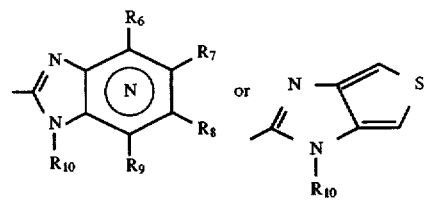

and
X is

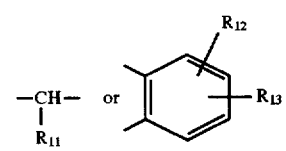

wherein:
N in the benzimidazole moiety of Het₂ means that one of the carbon atoms substituted by any one of $R_6$ to $R_9$ is exchanged for an unsubstituted nitrogen atom;

$R_1$, $R_2$ and $R_3$ are the same or different and selected from the group consisting of hydrogen, alkyl, alkoxy which is unsubstituted or substituted by fluorine, alkylthio, alkoxyalkoxy, dialkylamino, piperidino, morpholino, halogen, phenylalkyl and phenylalkoxy;

$R_4$ and $R_4$ are the same or different and selected from the group consisting of hydrogen, alkyl and aralkyl;

$R_5$ is hydrogen, halogen, trifluoromethyl, alkyl or alkoxy;

$R_6$-$R_9$ are the same or different and selected from the group consisting of hydrogen, alkyl, alkoxy, halogen, haloalkoxy, alkylcarbonyl, alkoxycarbonyl, oxazolyl and trifluoroalkyl;

or adjacent groups among substituents $R_6$-$R_9$ together with the carbon atoms to which they are attached form an unsubstituted or a substituted ring;

$R_{10}$ is hydrogen or alkoxycarbonyloxymethyl;

$R_{11}$ is hydrogen or forms an alkylene chain together with $R_3$;

$R_{12}$ and $R_{13}$ are the same or different and selected from the group consisting of hydrogen, halogen and alkyl;

which method comprises the steps of:
enantioselectively bioreducing a racemic sulfoxide compound of the formula (II) to the corresponding sulfide compound of formula (I):

Het₁-X-S-Het₂    (I)

by means of a microbial organism or a microbial enzyme system; and isolating the pharmaceutically active single enantiomeric or enantiomerically enriched sulfoxide compound.

2. A method according to claim 1 wherein:
Het₁ is

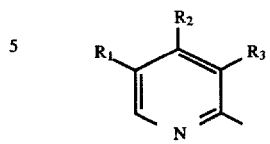

and
Het₂ is

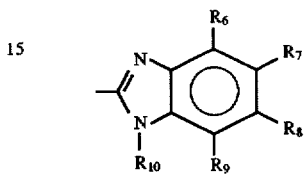

and
X is

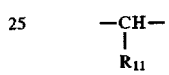

3. A method according to claim 1 or 2 wherein the compound of formula (II) is a H⁺K⁺-ATPase enzyme inhibitory compound of formula:

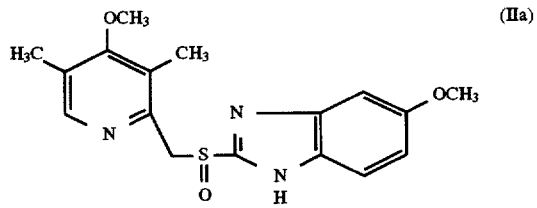
(IIa)

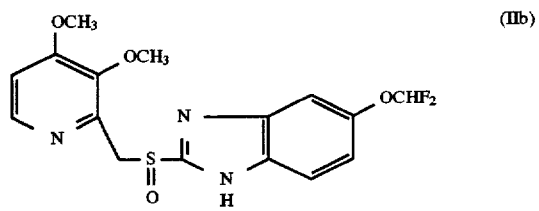
(IIb)

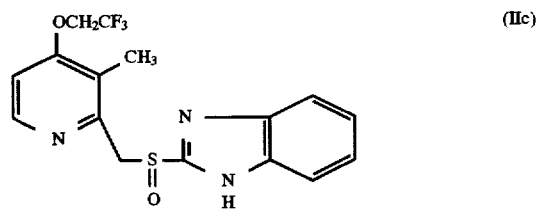
(IIc)

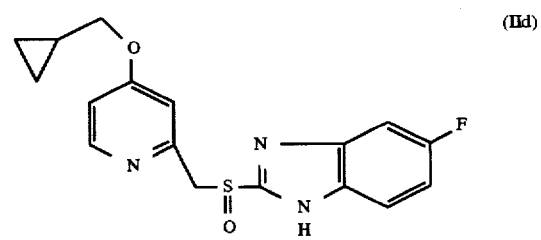
(IId)

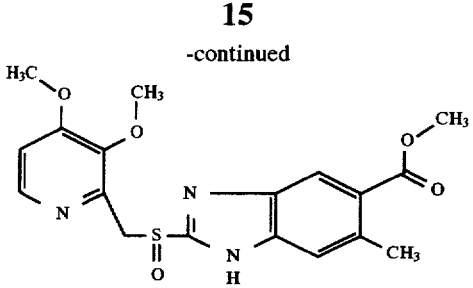

(IIe)

4. A method according to any one of the previous claims wherein a single enantiomer of the compound of formula (II) is obtained.

5. The method according to claim 3, wherein the racemic sulfoxide compound of formula (IIa) is enantioselectively bioreduced to an enantiomeric or enantiomerically enriched sulfide form of formula (Ia) which is effected by the action of *Proteus vulgaris, Proteus mirabilis, Escherichia coli, Rhodobacter capsulatus* or a DMSO reductase isolated from *R. capsulatus*; and separated from the sulfoxide racemate.

6. The method according to claim 3, wherein the racemic sulfoxide compound of formula (IIb) is enantioselectively bioreduced to an enantiomeric or enantiomerically enriched sulfide form of formula (Ib) which is effected by the action of *Escherichia coli*; and separated from the sulfoxide racemate.

7. The method according to claim 3, wherein the racemic sulfoxide compound of formula (IIc) is carried out enantioselectively bioreduced to an enantiomeric or enantiomerically enriched sulfide which is effected by the action of *Escherichia coli*; and separated from the sulfoxide racemate.

8. The method according to claim 3, wherein the racemic sulfoxide compound of formula (IId) or (IIe) is enantioselectively bioreduced to an enantiomeric or enantiomerically enriched corresponding sulfide compound of formula (Id) or (Ie) respectively by the action of of *Proteus mirabilis* or *Escherichia coli*; and separated from the sulfoxide racemate.

9. A method for the preparation of a pharmaceutically active enantiomeric or enantiomerically enriched sulfoxide compound of formula II as defined in any one of the claims 1–3, comprising the steps of:

(a) enantioselectively bioreducing a racemate sulfoxide compound to its sulfide form of formula I as defined using whole cells of *A. coli* ATCC 33694, *P. vulgaris* NCI MB67, *P. mirabilis* NCI MB 8268, or using a preparation of DMSO reductase enzyme from *Rhodobacter capsulatus* DSM938; and (b) isolating the pharmaceutically active enantiomeric or enantiomerically enriched sulfoxide compound.

* * * * *

UNITED STATES PATENT AND TRADEMARK OFFICE
CERTIFICATE OF CORRECTION

PATENT NO. : 5,776,765
DATED : July 7, 1998
INVENTOR(S) : Graham et al.

It is certified that error appears in the above-indentified patent and that said Letters Patent is hereby corrected as shown below:

Claim 1 at column 13, line 41: the second appearance of "$R_4$" should be -- $R_{4'}$ --.

Claim 7 at column 15, line 28: delete "carried out".

Signed and Sealed this

Sixth Day of July, 1999

Attest:

Q. TODD DICKINSON

*Attesting Officer*    Acting Commissioner of Patents and Trademarks